United States Patent [19]

McDonald et al.

[11] Patent Number: 6,072,576
[45] Date of Patent: *Jun. 6, 2000

[54] ON-LINE CONTROL OF A CHEMICAL PROCESS PLANT

[75] Inventors: Michael F. McDonald, Kingwood; Robert L. Long, Houston, both of Tex.; Carl J. Thomas, Baton Rouge, La.

[73] Assignee: Exxon Chemical Patents Inc., Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/986,971

[22] Filed: Dec. 8, 1997

Related U.S. Application Data

[60] Provisional application No. 60/034,614, Dec. 31, 1996.

[51] Int. Cl.[7] .................. G01J 3/42; G01J 3/44; G01N 21/35
[52] U.S. Cl. .......... 356/300; 356/301; 250/339.08; 250/339.12; 702/28
[58] Field of Search ............... 356/300, 301; 250/339.12, 339.08; 702/22, 28

[56] References Cited

U.S. PATENT DOCUMENTS

| | | |
|---|---|---|
| 3,553,295 | 1/1971 | Bean et al. ............... 260/879 |
| 4,701,838 | 10/1987 | Swinkels et al. ........ 364/164 |
| 4,830,757 | 5/1989 | Lynch et al. . |
| 5,116,915 | 5/1992 | Mamedov et al. ........ 526/60 |
| 5,121,337 | 6/1992 | Brown . |
| 5,155,184 | 10/1992 | Laurent et al. ............ 526/59 |
| 5,243,546 | 9/1993 | Maggard . |
| 5,446,681 | 8/1995 | Gethner et al. . |
| 5,532,487 | 7/1996 | Brearley et al. ........ 250/339.12 |

FOREIGN PATENT DOCUMENTS

WO 84/01430 4/1984 WIPO .
WO 96/11400 4/1996 WIPO .

OTHER PUBLICATIONS

B. Buchanan et al, "Trends in near–infrared analysis", pp. 154–157, Trends in Analytical Chemistry, vol. 5, No. 6, 1986.

D.E. Honigs et al., "Near Infrared Determination of Several Physical Properties of Hydrocarbons", Analytical Chemistry, pp. 443–445, vol. 57, No. 2, Feb. 1985.

J.M. Chalmer, "The development and value of computer–aided infrared spectroscopy on process control measurements ", pp. 51–59, (undated).

Ildilco E. Frank et al, "Prediction of Product Quality from Spectral Data Using the Partial Least–Squares Method", J. Chem.Inf.Comput.Sci., vol. 24, No. 1, pp. 20–24, 1984.

*Primary Examiner*—F. L. Evans
*Attorney, Agent, or Firm*—Douglas J. Collins; Andrew B. Griffis

[57] ABSTRACT

A process plant for the manufacture of halobutyl rubber is provided with online monitoring and control of the process parameters to control the properties of the product. It incorporates an in-situ measurement system that does not require the removal of any sample material from the process. It uses a Fourier Transform Near Infrared (FTNIR) spectrometer, fiber-optic cables, a viscometer for measuring solution viscosity and a Resistance Temperature Device (RTD) for temperature measurement. An online real-time analyzer system using a Constrained Principal Spectral Analysis program predicts the property of the polymer product and provides the process control system with analysis of the data using derived relationships between the physical properties of the polymer and these spectral measurements and the measured values of fluid viscosity and temperature. Differences between the predicted and desired property of the product are used to control process parameters. The method can be used for a variety of chemical process plants.

54 Claims, 5 Drawing Sheets

ON-LINE CONTROL OF A CHEMICAL PROCESS PLANT

This application claims the benefit of U.S. Provisional Application No. 60/034,614 filed on Dec. 31, 1996.

FIELD OF THE INVENTION

The invention relates to a chemical plant and to a method of controlling chemical processes in a chemical plant. More particularly, the invention relates to a method for controlling Mooney viscosity, polymer unsaturation, comonomer incorporation, halogen content, molecular weight and molecular weight distribution during polymerization or halogenation process of isolefin copolymers and multiolefins, in particular butyl rubber.

DESCRIPTION OF THE RELATED ART

A prominent method for controlling the polymerization of olefins in a medium of inert solvents or diluents involves measuring the concentration of polymer in the medium and the viscosity of the polymer solution in order to calculate a single variable—the "Mooney viscosity." The Mooney viscosity then is used as the single variable by which the entire process is controlled.

"Single variable" process control works well where the quality of the desired product is directly proportional to only one variable. "Single variable" process control does not work well where two or more variables are directly related to product quality. For example, the quality of butyl rubber is directly related to both Mooney viscosity and molecular weight distribution within the polymer solution during processing.

Various attempts have been made to provide additional process control for the production of butyl rubber based on the molecular weight distribution of the polymer as well as on Mooney viscosity. Unfortunately, the methods used to date either have been inefficient or have been based on insufficiently comprehensive data to effectively control the process on the basis of molecular weight as well as Mooney viscosity.

A need exists for an efficient and precise method to control the production of butyl rubber using both Mooney viscosity and polymer molecular weight as process control parameters.

SUMMARY OF THE INVENTION

The invention is a method for online control of a process plant having a plurality of steps producing a product with a property P having a desired value D. It obtains a set of measured spectra for a set of calibration samples at at least one intermediate step in the process and removes the effect of measurement errors for the calibration samples to produce a set of corrected spectra for the set of calibration samples. A set of weights relating the corrected spectrum of each of the calibration samples to a set of eigenspectra are determined, giving a matrix of weights. A value of the property P of the finished product for each of the calibration samples is obtained. Next, a predictive model relating the value of the property P of the product for the calibration samples to the set of weights is derived. Next, a spectrum for a test sample at the intermediate step in the process is measured and corrected for measurement errors. A value for the property P for the test sample is predicted from a predictive model that uses the set of weights derived from the calibration samples and the corrected spectrum of the test sample. The difference between this predicted value and the desired value is used for controlling the process. Optionally, measurements may be made in addition to the spectra and used in the derivation of the predictive model and the predictive process.

DETAILED DESCRIPTION OF THE INVENTION

The invention is best understood by reference to the accompanying FIGS. 1–5 illustrating the preferred embodiment of the invention.

The bulk of the world production of butyl rubber is made by a precipitation (slurry) polymerization process in which isobutylene and a minor amount of isoprene are copolymerized using aluminum chloride in methyl chloride diluent at $-100$ to $-90°$ C. Halogenated butyl rubbers are produced commercially by dissolving butyl rubber in a hydrocarbon solvent and contacting the solution with elemental halogens.

Figure 1:
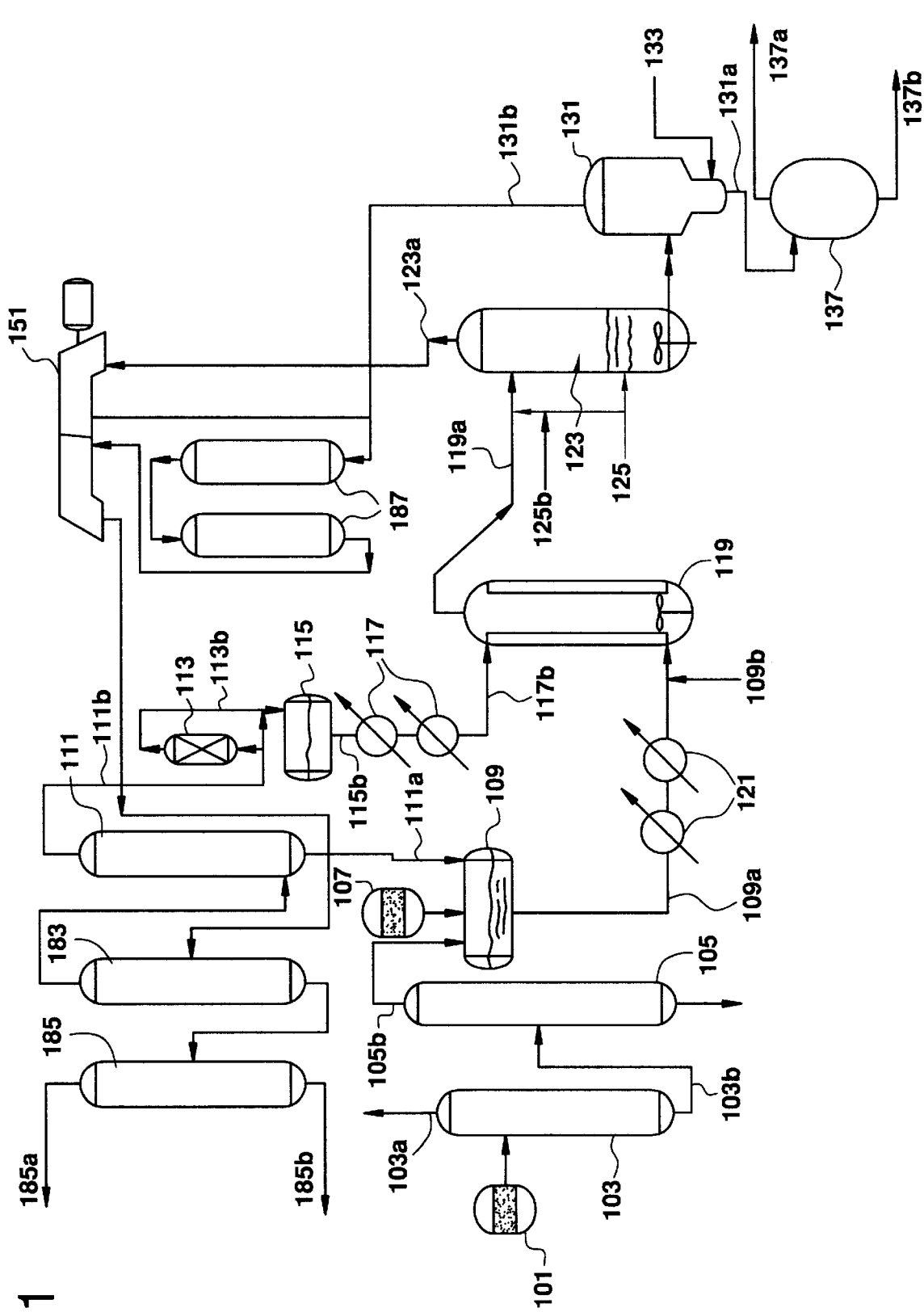
FIG. 1 is a simplified flow diagram of a plant for butyl rubber polymerization.

FIG. 1 is a simplified flow diagram of the polymerization section of a slurry process. Isobutylene 101 is dried and fractionated in a drying tower 103. The water 103a is removed and the fraction consisting of isobutylene, 2-butenes and high boiling components 103b is purified in the isobutylene purification tower 105. The feed blend drum 109 blends a feed consisting of 25–40% by weight of isobutylene 105b, 0.4–1.4% by weight of isoprene 107 (depending upon the grade of butyl rubber to be produced) and recycled methyl chloride 111a from a methyl chloride purification tower 111. Coinitiator solution is produced by passing pure methyl chloride 111b through beds 113 of granular aluminum chloride at 30–45° C. This concentrated solution 113b is diluted with additional methyl chloride and stored in drum 115. The diluted mixture is chilled in catalyst chillers 117 to a temperature of $-100$ to $-90°$ C. The chilled coinitiator 117b is fed to the reactor 119. The reactor comprises a central vertical draft tube surrounded by concentric rows of cooling tubes. The reactor is mixed by an axial flow pump located at the bottom of the draft tube that circulates slurry through the cooling tubes. The copolymerization reaction is exothermic, releasing approximately 0.82 MJ/kg of polymer (350 Btu/lb). The heat is removed by exchange to boiling ethylene supplied as liquid to jackets that enclose the tube section of the reactor. The reactor is constructed of alloys that have adequate impact strength at the low temperature of the polymerization reaction. As shown in FIG. 1, the blended feed 109a is chilled by feed chillers 121 and fed into the reactor 119. A branching agent 109b may be added to the blended feed 109a to control the properties of the polymer formed in the reactor 119. The output of the reactor 119a consists of butyl rubber, methyl chloride and unreacted monomers. Warm hexane and hexane vapor 125 and a quench agent 125b are added to the reactor outlet line 119a and solution drum 123 and most of the methyl chloride and unreacted monomers are vaporized and sent to the recycle gas compressor 151. The butyl rubber solution in liquid hexane is fed to the cement stripper 131 where hot hexane vapor is added 133. The hot cement 131a from the bottom of the cement stripper 131 contains the polymer in solution in hexane. The hot cement 131a flows through the flash concentrator 137 where cement is concentrated by vaporizing a portion of the hexane in stream 131a. The flushed hexane is recycled to the solution drum 123, and the output 137b of the flash concentrator is the feed for halogenation, described below with reference to FIG. 2. All the Methyl chloride, monomers and a minor amount of hexane 131b from the cement stripper are recycled. 151 is a recycle gas compressor that, in association with dryers 187, methyl chloride purification tower 111, recycle tower 183 and purge tower 185 recycles the methyl chloride 111a and isobutylene 185a. Stream 185b is purged from the process.

Figure 2:
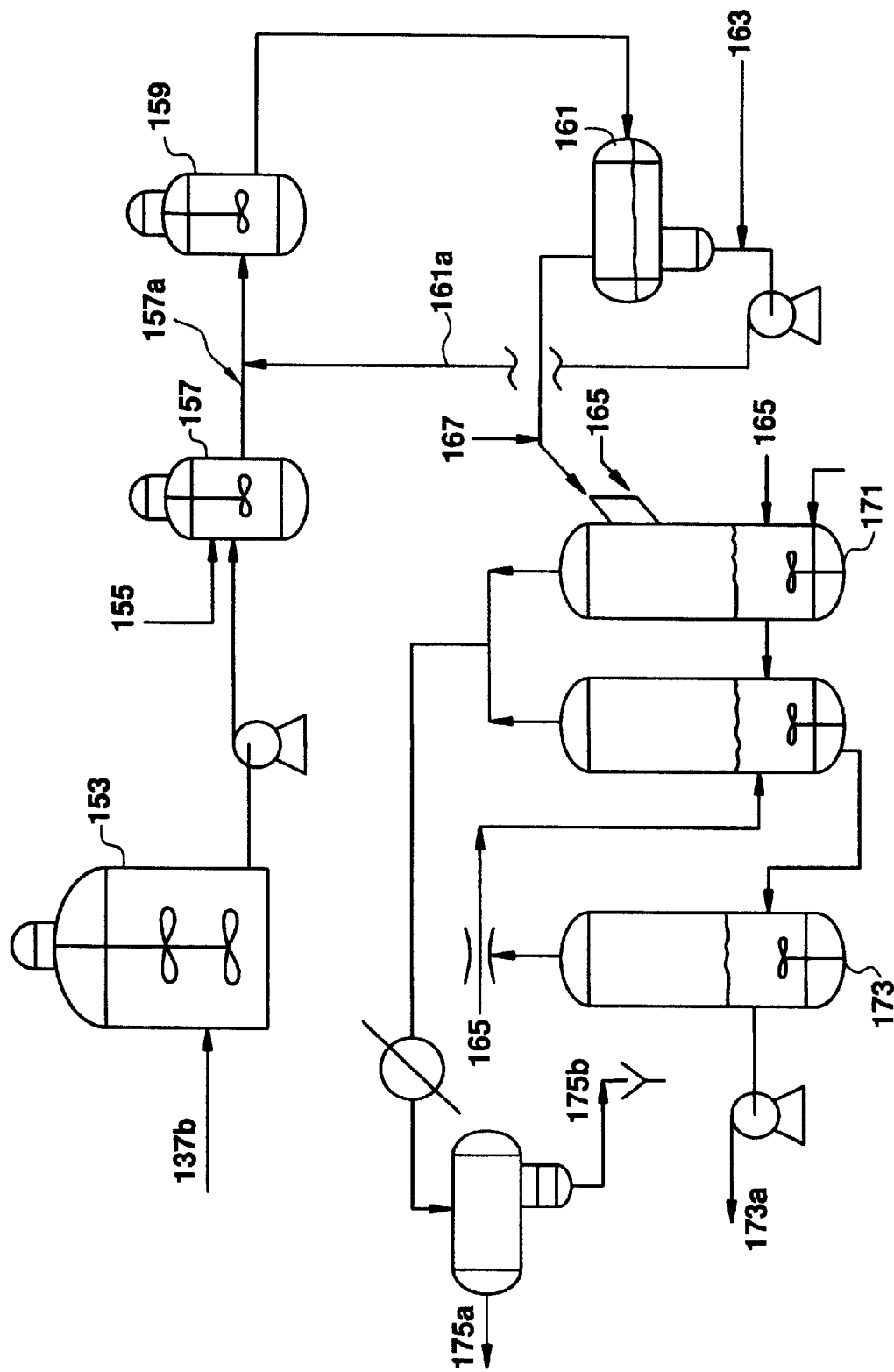
FIG. 2 is a simplified flow diagram of a plant for halogenation of butyl rubber.

In the halogenation process shown in FIG. 2, the butyl rubber solution 137b is stored in tanks 153. The solution reacts with chlorine or bromine 155 in one or more highly agitated reaction vessels 157 at 30–60° C. For safety reasons, chlorine is introduced as a vapor or in dilute solution because liquid chlorine reacts violently with the butyl rubber solution. However, bromine may be used in liquid or vapor form because of its lower reaction rate. The halogenation by-product of HCl or HBr is neutralized with dilute aqueous caustic 163 in high intensity mixers 159. Antioxidants and stabilizers 167 such as calcium stearate and epoxized soybean oil are added. The solution is sent to a multi vessel solvent-removal system 171 where steam and water 165 vaporize the solvent and produce crumb like rubber particles in water. The final solvent content and the steam usage for solvent removal depends on the conditions in each vessel. Typically, the lead flash drum is operated at 105–120 0 C. and 200–300 kPa (2–3 atm). Conditions in the final stripping stage 173 are 101° C. and 105 kPa (1.04 atm). The hexane 175a is recycled while the halobutyl slurry 173a is sent on for finishing.

Figure 3:
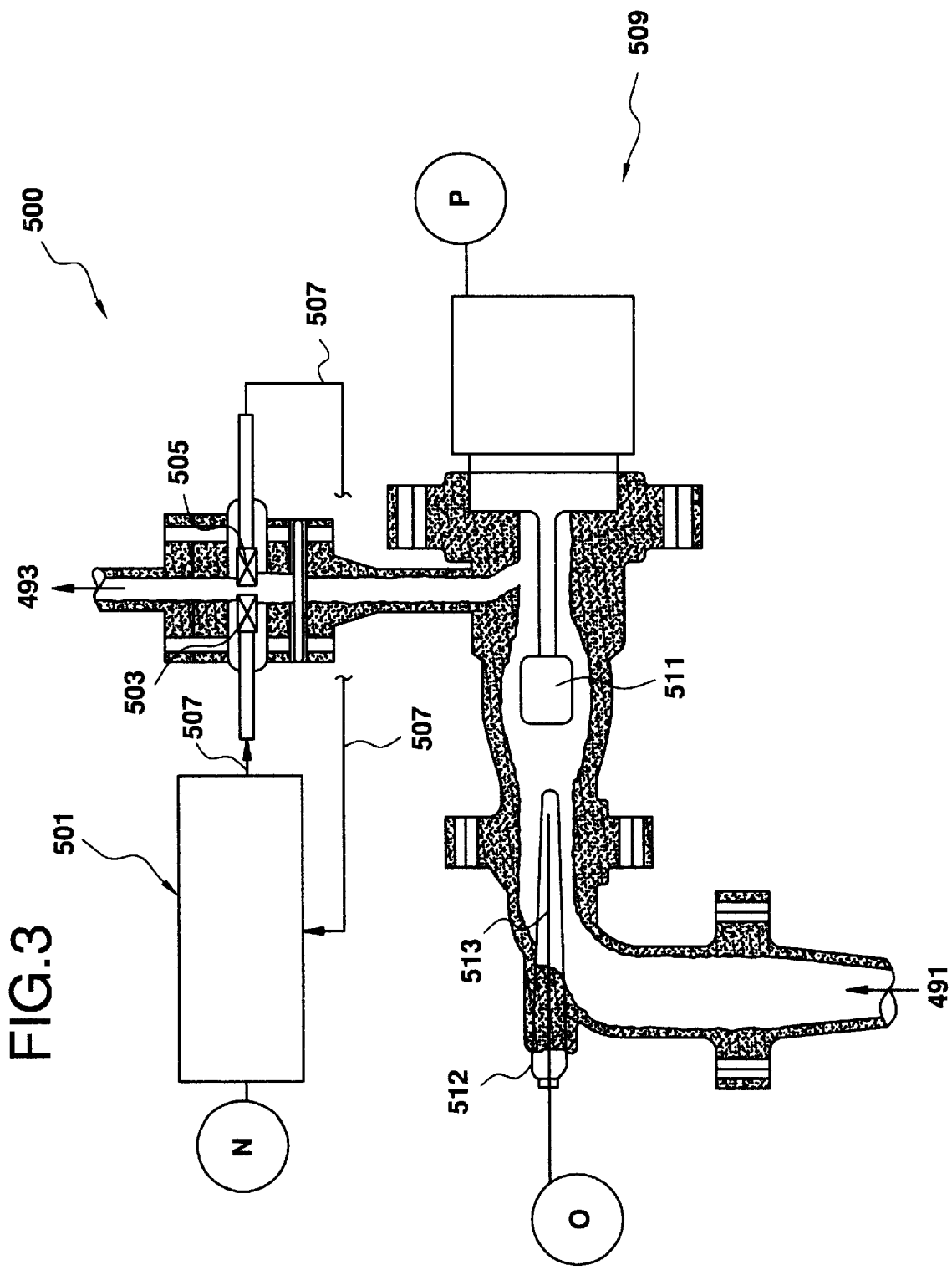
FIG. 3 illustrates the equipment used in the instrumentation and control of the process.

FIG. 3 is an illustration of an apparatus useful in the present invention for online monitoring of a flow stream in a manner that enables a prediction of the properties of the finished product. This prediction is, in turn, used to manipulate the inputs and the operating conditions of the equipment to obtain finished products with the desired properties.

The instrumentation assembly 500 is generally mounted so as to monitor fluids in the flow stream of the process. As discussed above, in one embodiment of the invention, this is done at the output to the cement stripper 131 to monitor the cement solution 131a (FIG. 1) and to monitor the output 157a after halogenation (FIG. 2). At the output of the cement stripper 131, the measurements are used to determine Mooney viscosity, Unsaturation and Molecular Weight Distribution. while at the output 157a after halogenation (FIG. 2), the measurements are used to predict the Halogen content of the finished product. Flow into the instrumentation assembly is indicated at 491 while the outflow is indicated at 493, with the direction of flow of the fluids in the process stream as indicated. In the preferred embodiment of the invention, the assembly comprises a spectrometer, a viscometer and a temperature measurement device. In FIG. 3, the spectrometer is shown at 501. In the preferred embodiment, it is a Fourier Transform Near Infrared (FTNIR) spectrometer. As the name suggests, FTNIR is a spectrometer designed to make measurements in the near infrared region and includes appropriate microprocessors (not shown) to compute Fourier Transforms of the input data. A fiber optic link 507 from the FTNIR spectrometer sends an infrared signal across the flow stream between the gap 503–505. The output of the FTNIR spectrometer is spectral data N detailing the absorption spectra of the fluid being monitored and is used by the process control computer, not shown, as described below.

The instrumentation also includes a viscometer, indicated at 509, that has a probe 511 in the fluid flow stream. The probe measures the viscosity product (product of viscosity and density) of the fluid in the flow stream. The viscosity product measurements are output at P for use by the process control computer, not shown.

The next component of the instrumentation is a temperature measuring device 511 that comprises a probe 513 that monitors the temperature of the fluid in the flow stream. The output of the temperature measuring device is a temperature measurement O of the temperature of the fluid in the flow stream. The temperature measurement O is used by the process control computer, not shown, as described below.

In a preferred embodiment, the path length for the infrared signal is approximately 0.8 mm. This path length greatly reduces the need to compensate the absorption spectra for changes in the path length compared to conventional methods where the path length is much smaller.

The components of the instrumentation (the temperature measuring device, viscometer and spectrometer) are not discussed in detail as they would be familiar to those knowledgeable in the art.

The outputs N, O and P of the instrumentation assembly are transmitted to a computer that analyzes the measurements, as discussed below, and predicts properties of the finished product that could be expected from the process. Differences between the predicted and desired properties of the product are used to control the process parameters, also as discussed below.

The three measuring instruments disclosed here (spectrometer, viscometer and temperature gauge) are for illustrative purposes only. Those knowledgeable in the art would recognize that other measurements could also be made. These additional measurements are intended to be within the scope of the present invention.

ANALYSIS OF DATA

Brown (U.S. Pat. No. 5,121,337) discloses a method for correcting spectral data for data due to the spectral measurement process itself and estimating unknown property and/or composition data of a sample using such method. This patent is incorporated here by reference and forms the basis for the analysis of the spectral data derived from the FTNIR spectrometer.

As disclosed by Brown, the first step of the analysis is that of calibration. The spectral data for n calibration samples is quantified at f discrete frequencies to produce a matrix X (of dimension f×n) of calibration data. The first step in the method involves producing a correction matrix $U_m$ of dimension f×m comprising m digitized correction spectra at the discrete frequencies f, the correction spectra simulating data arising from the measurement process itself. The next step involves orthognalizing X with respect to $U_m$ to produce a corrected spectral matrix $X_c$ whose spectra are orthogonal to all the spectra in $U_m$. Due to this orthogonality, the spectra in matrix $X_c$ are statistically independent of spectra arising from the measurement process itself.

The spectra can be absorption spectra and preferred embodiments described below all involve measuring absorption spectra. However, this is to be considered as exemplary and not limiting on the scope of the invention as defined by the appended claims, since the method disclosed herein can be applied to other types of spectra such as reflection spectra and scattering spectra (such as Raman scattering). Although the description given herein and with reference to the drawings relate to NIR (near-infrared) and MIR (mid-infrared), nevertheless, it will be understood that the method finds applications in other spectral measurement wavelength ranges including, for example, ultraviolet, visible spectroscopy and Nuclear Magnetic Resonance (NMR) spectroscopy.

Generally, the data arising from the measurement process itself are due to two effects. The first is due to baseline variations in the spectra. The baseline variations arise from a number of causes such as light source temperature variations during the measurement, reflectance, scattering or absorption by the cell windows, and changes in the temperature (and thus the sensitivity) of the instrument detector. These baseline variations generally exhibit spectral features which are broad (correlate over a wide frequency range). The second type of measurement process signal is due to ex-sample chemical compounds present during the measurement process, which give rise to sharper line features in the spectrum. For current applications, this type of correction generally includes absorptions due to water vapor and/or carbon dioxide in the atmosphere in the spectrometer. Absorptions due to hydroxyl groups in optical fibers could also be treated in this fashion. Corrections for contaminants present in the samples can also be made, but generally only in cases where the concentration of the contaminant is sufficiently low as to not significantly dilute the concentrations of the sample components, and where no significant interactions between the contaminant and sample component occurs. It is important to recognize that these corrections are for signals that are not due to components in the sample. In this context, "sample" refers to that material upon which property and/or component concentration measurements are conducted for the purpose of providing data for the model development. By "contaminant", we refer to any material which is physically added to the sample after the property/component measurement but before or during the spectral measurement.

In a preferred way of performing the invention, in addition to matrix X of spectral data being orthogonalized relative to the correction matrix $U_m$, the spectra or columns of $U_m$ are all mutually orthogonal. The production of the matrix $U_m$ having mutually orthogonal spectra or columns can be achieved by first modeling the baseline variations by a set of orthogonal frequency (or wavelength) dependent polynomials, which are computer generated simulations of the baseline variations and form the matrix $U_p$, and then at least one, and usually a plurality, of spectra of ex-sample chemical compounds (e.g. carbon dioxide and water vapor) which are actual spectra collected on the instrument, are supplied to form the matrix $X_s$. Next the columns of $X_s$ are orthogonalized with respect to $U_p$ to form a new matrix $X_{s'}$. The preceding steps remove baseline effects from ex-sample chemical compound corrections. Then, the columns of $X_{s'}$ are orthogonalized with respect to one another to form a new matrix $U_s$, and lastly $U_p$ and $U_s$ are combined to form the correction matrix $U_m$, whose columns are the columns of $U_p$ and $U_s$ arranged side-by-side. It would be possible to change the order of the steps such that the columns of $X_s$ are first orthogonalized to form a new matrix of vectors and then the (mutually orthogonal) polynomials forming the matrix $U_p$ are orthogonalized relative to these vectors and then combined with them to form the correction matrix $U_m$. However, this changed order is less preferred because it defeats the advantage of generating the polynomials as being orthogonal in the first place, and it will also mix the baseline variations in with the spectral variations due to ex-sample chemical compounds and make them less useful as diagnostics of instrument performance.

Once the matrix X (dimension f×n) has been orthogonalized with respect to the correction matrix $U_m$ (dimension f×m), the resulting corrected spectral matrix $X_c$ will still contain noise data. The noise can be removed in the following way. Firstly, a singular value decomposition is performed on matrix $X_c$ in the form $X_c = U\Sigma V^t$, where U is a matrix of dimension f×n and contains the principal component spectra as columns, $\Sigma$ is a diagonal matrix of dimension n×n and contains the singular values, and V is a matrix of dimension n×n and contains the principal component scores, Vt being the transpose of V. In general, the principal components that correspond to noise in the spectral measurements in the original n samples will have singular values which are small in magnitude relative to those due to the wanted spectral data, and can therefore be distinguished from the principal components due to real sample components. Accordingly, the next step in the method involves removing from U, $\Sigma$ and V the k+1 through n principal components that correspond to the noise, to form the new matrices U', $\Sigma'$ and V' of dimensions f×k, k×k and n×k, respectively. When these matrices are multiplied together, the resulting matrix, corresponding with the earlier corrected spectra matrix $X_c$, is free of spectral data due to noise.

For the selection of the number (k) of principal components to keep in the model, a variety of statistical tests suggested in the literature could be used but the following steps have been found to give the best results. Generally, the spectral noise level is known from experience with the instrument. From a visual inspection of the eigenspectra (the columns of matrix U resulting from the singular value decomposition), a trained spectroscopist can generally recognize when the signal levels in the eigenspectra are comparable with the noise level. By visual inspection of the eigenspectra, an approximate number of terms, k, to retain can be selected. Models can then be built with, for example, k−2, k−1, k, k+1, k+2 terms in them and the standard errors and PRESS (Predictive Residual Error Sum of Squares) values are inspected. The smallest number of terms needed to obtain the desired precision in the model or the number of terms that give the minimum PRESS value is then selected. The selection of the number of steps is made by the spectroscopist, and is not automated. A Predicted Residual Error Sum of Squares is calculated by applying a predictive model for the estimation of property and/or component values for a test set of samples which were not used in the calibration but for which the true value of the property or component concentration is known. The difference between the estimated and true values is squared, and summed for all the samples in the test set (the square root of the quotient of the sum of squares and the number of test samples is sometimes calculated to express the PRESS value on a per sample basis). A PRESS value can be calculated using a cross validation procedure in which one or more of the calibration samples are left out of the data matrix during the calibration, and then analyzed with the resultant model, and the procedure is repeated until each sample has been left out once.

The method further requires that c properties and or/composition data be collected for each of the n calibration samples to form a matrix Y of dimension n×c where c≧1. For each of the calibration samples, the corresponding column of $X_c$ is represented by a weighted combination of the principal components (the columns of $\Sigma$). These weights are called the "scores" and are denoted by $s_i$. A regression relation is then determined between the property (dependent variable) and a combination of the "scores" and other measurements (independent variables). The additional measurements that have been used in the present invention are the viscosity product (product of viscosity and density, denoted by $v\rho$) and the temperature t. Once these regression coefficients have been determined, they are used as part of the online prediction process. In the prediction process, the measured spectra are corrected for background effects as discussed above and the "scores" with the determined principal components calculated. The scores, the measured viscosity product and temperature, and the regression coefficients derived in the calibration process give a prediction of the property under consideration.

It has been found that the Mooney viscosity can be accurately predicted (within 1 unit) using the FTNIR spectral measurements along with the viscosity product and the temperature. This is a considerable improvement over prior art. The unsaturation content and halogen content can be accurately predicted by direct correlation with the FTNIR spectra.

Those versed in the art would recognize that the eigenspectra obtained by this invention through the singular value decomposition form a set of orthonormal basis functions for the range of wavelengths used: any member of an orthonormal set of basis functions has a dot product of unity with itself and zero with any other member of the orthonormal set of basis functions. Other orthonormal basis functions could also be used in the derivation of the predictive model including Legendre polynomials and trigonometric functions (sines and cosines). The use of other orthonormal basis functions is intended to be within the scope of the present invention.

Figure 4:
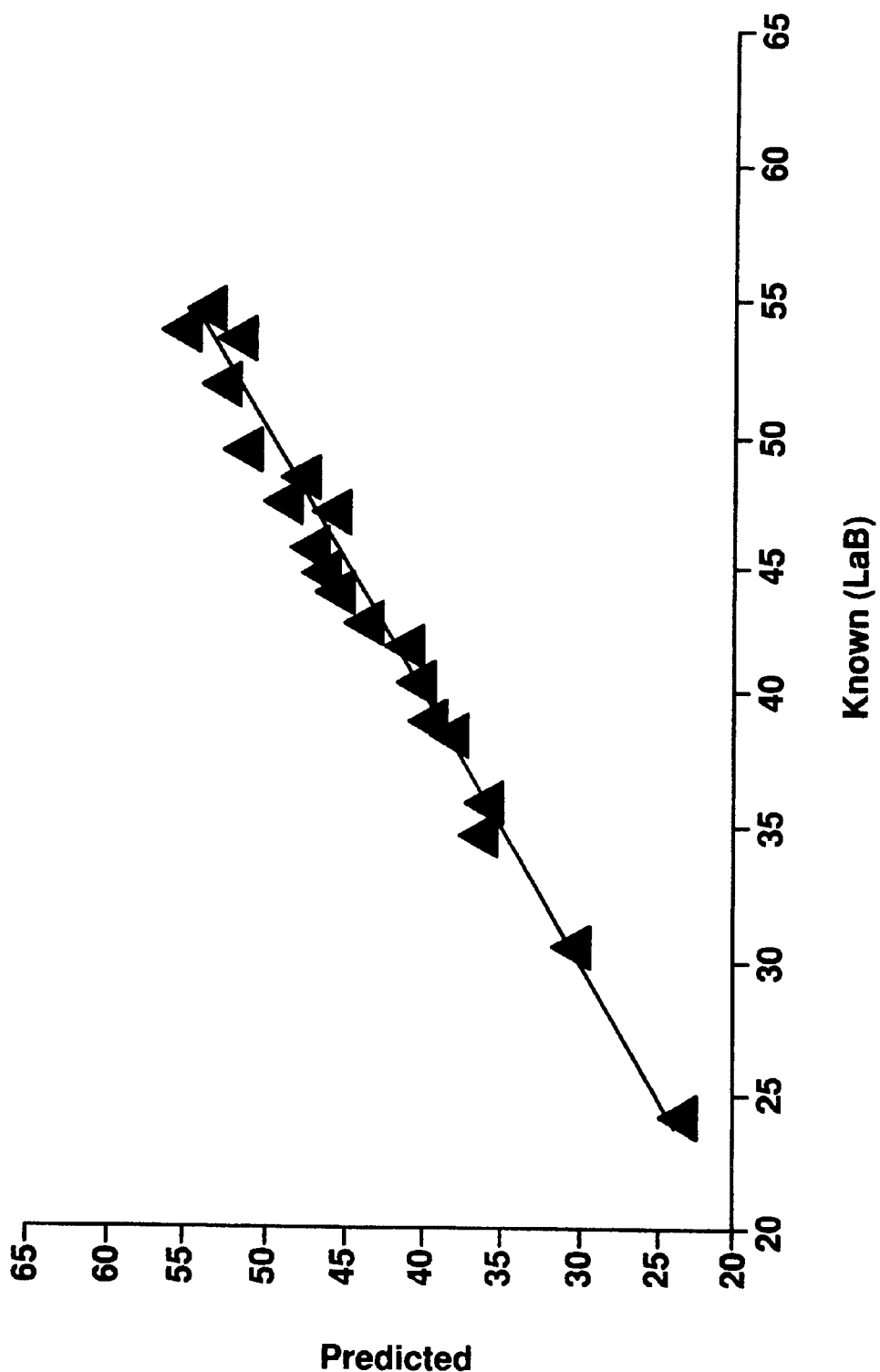
FIG. 4 is a comparison of the measured and predicted Mooney viscosity according to the method of this invention.

FIG. 4 shows a comparison of results of prediction of Mooney viscosity from the FTNIR spectral measurements and the measurements of viscosity product and temperature. The abscissa is the measured Mooney viscosity of laboratory samples while the ordinate is the predicted Mooney viscosity based on the regression relations. As can be seen the fit is very good with a standard error of prediction less than one unit.

Figure 5:
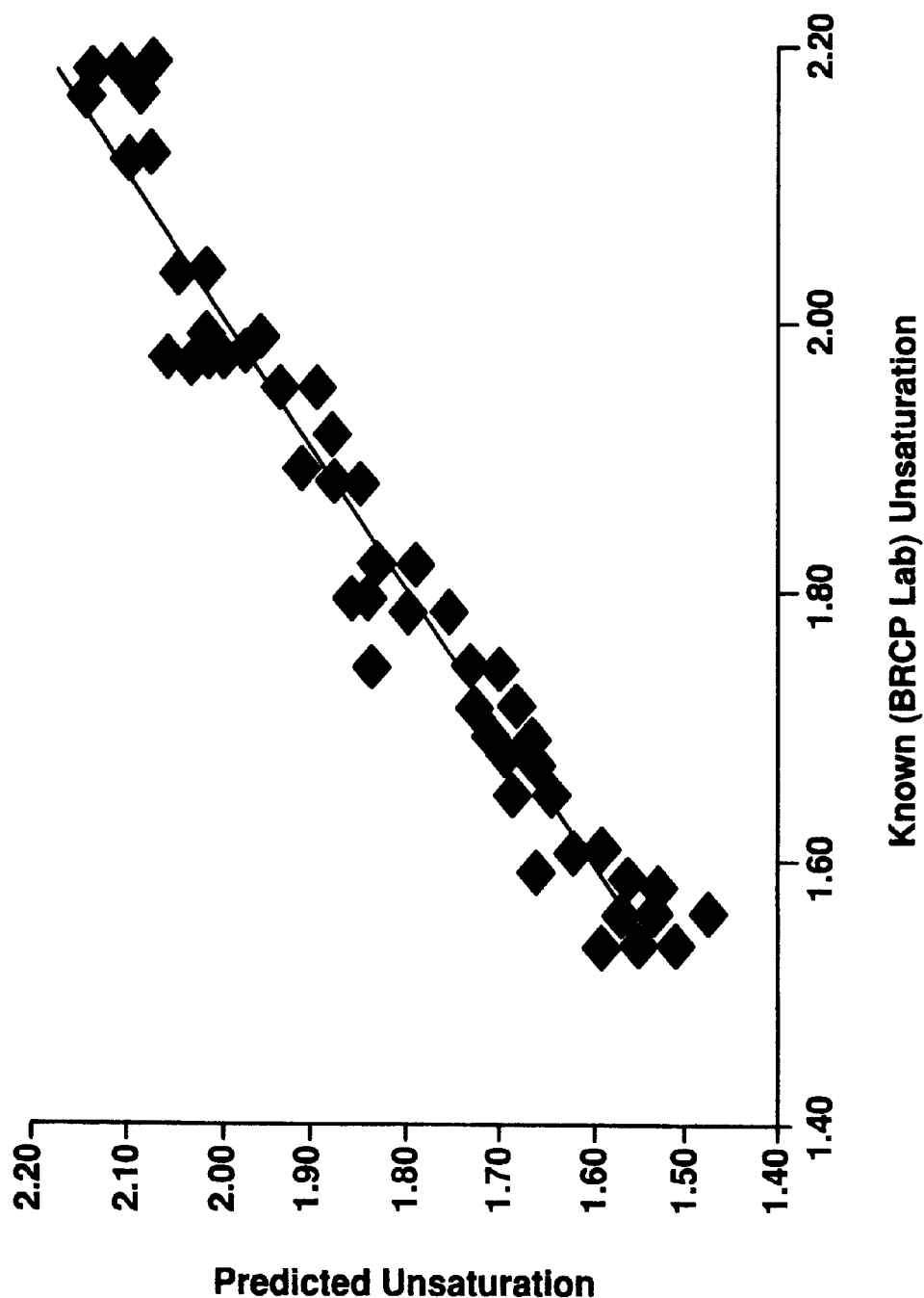
FIG. 5 is a comparison of the measured and predicted unsaturation according to the method of this invention.

FIG. 5 is a similar plot comparing the predictions of unsaturation of halobutyl rubber with known values of unsaturation based on spectral measurements only. The abscissa is the measured laboratory value of the halobutyl rubber unsaturation content while the ordinate is the predicted value of the halobutyl unsaturation from a regression of the spectral value.

The predictions made as in FIGS. 4 and 5 are accurate enough to be able to provide feedback control of these properties, described below.

PROCESS CONTROL

The in-situ determination of Mooney viscosity made by the method described above can be used as input to a controller that manipulates the catalyst addition or coinitiator rate at 117b in FIG. 1. Unsaturation can be controlled by using the in-situ saturation measurement to a controller that manipulates the isoprene content of the feed 107 in FIG. 1. Comonomer incorporation can be controlled by using the in-situ comonomer content as the input to a controller that manipulates the butyl reactor feed comonomer that in a preferred embodiment is isoprene 107. Molecular weight distribution can be controlled by using the in-situ molecular weight distribution as the input to a controller that manipulates the quench flow 125b and/or branching agent 109b flow to the butyl reactor. Butyl reactor halogen content can be controlled by using the ins-situ halogen content measurement as the input to a controller that manipulates the halogen flow to a butyl halogenation reactor (155 in FIG. 2).

The example given above is for illustrative purposes only. The invention can be used for a wide variety of processes and manufacturing plants. The processes for which the method can be used include, but are not limited to polymerization, steam cracking, olefin purification, aromatic purification, isomerization, catalytic cracking, catalytic reforming, hydrogenation, oxidation, partial oxidation, dehydration, hydration, nitration, epoxidation, distillation, combustion, alkylation, neutralization, ammination, esterification, dimerization, membrane separation, carbonylation, ketonization, hydroformulation, oligomerization, pyrolysis, solfonation, crystallization, adsorption, extractive distillation, hydrodealkylation, dehydrogenation, aromatization, cyclization, thermal cracking, hydrodesulphurization, hydrodenitrogenation, peroxidation, deashing and halogenation. The properties that are controlled could include Mooney viscosity, polymer unsaturation, comonomer incorporation, halogen content, polymer concentration, monomer concentration, molecular weight, melt index, stream component composition, moisture in the product, and molecular weight distribution. Depending upon the process, the in situ measurement made in addition to the spectral measurements could include, among others, temperature, viscosity, pressure, density, refractive index, pH value, conductance and dielectric constant.

These and other similar variations in the process, property being controlled and measurements made for prediction of the property being controlled are intended to be within the scope of the invention.

What is claimed is:

1. A method for online control of a process to produce a product with a property P having a desired value D comprising:

obtaining a set of measured spectra having measurement errors for a set of calibration samples at at least one intermediate step in said process;

correcting said measured spectra for said measurement errors to produce a set of corrected spectra for said set of calibration samples;

determining a set of weights relating said corrected spectrum of each of said calibration samples to a set of orthonormal basis functions;

obtaining a value of said property P for each of said calibration samples;

determining a predictive model relating said value for said property P to said set of weights;

measuring a spectrum for a test sample at said at least one intermediate step in said process;

obtaining a corrected spectrum for said test sample at said at least one intermediate step;

determining an estimated value E for said property P for said test sample from said predictive model and said corrected spectrum of said test sample; and controlling said process using a calculated difference between said estimated value E and said value D.

2. The method of claim 1 wherein said product comprises a polymer.

3. The method of claim 1 wherein said measured spectra are selected from the group consisting of: Raman spectra, NMR spectra, and infrared spectra.

4. The method of claim 1 wherein said measured spectra comprise absorbance spectra in the near infrared region.

5. The method of claim 4 wherein said predictive model is determined by a linear least squares regression.

6. The method of claim 3 wherein said process comprises a procedure chosen from the group consisting of: polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation; ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

7. The method of claim 4 wherein said process comprises a procedure chosen from the group consisting of: polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation; ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

8. The method of claim 6 wherein said set of orthonormal basis functions characterizing said corrected spectra for said calibration samples comprise eigenspectra determined by a Singular Value Decomposition.

9. The method of claim 7 wherein said set of orthonormal basis functions characterizing said corrected spectra for said calibration samples are eigenspectra determined by a Singular Value Decomposition.

10. The method of claim 8 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

11. The method of claim 9 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

12. The method of claim 9 wherein said measurement of near infrared spectra are made by a Fourier Transform Near Infrared (FTNIR) spectrometer.

13. The method of claim 11 wherein said measurement of near infrared spectra are made by a Fourier Transform Near Infrared (FTNIR) spectrometer.

14. The method of claim 10 wherein said measurement of said spectrum for said test sample is performed at least once every two minutes.

15. The method of claim 11 wherein the measurement of said spectrum for said test sample is performed at least once every two minutes.

16. A method for online control of a process to produce a product with a property P having a desired value D comprising:
    obtaining a set of measured spectra having measurement errors for a set of calibration samples at at least one intermediate step in the process;
    correcting said measured spectra for said measurement errors to produce a set of corrected spectra for said set of calibration samples;
    determining a set of weights relating said corrected spectrum of each of said calibration samples to a set of orthonormal basis functions obtaining a value of at least one additional property of said calibration samples;
    obtaining a value of said property P for each of said calibration samples, determining a predictive model relating said value for said property P to said set of weights and said value of said at least one additional property of said calibration samples;
    measuring a spectrum and said at least one additional property for a test sample at said at least one intermediate step in said process;
    obtaining a corrected spectrum for said test sample at said at least one intermediate step;
    determining an estimated value E for said property P for said test sample from said predictive model, said corrected spectrum and said value of said at least one additional property of said test sample; and
    controlling said process using a calculated difference between said estimated value E and said value D.

17. The method of claim 16 wherein said at least one additional property is selected from the group of: temperature, viscosity, pressure, density, refractive index, pH value, conductance and dielectric constant.

18. The method of claim 17 wherein said product comprises a polymer.

19. The method of claim 17 wherein said spectra are selected from the group consisting of: Raman spectra, NMR spectra, and infrared spectra.

20. The method of claim 17 wherein said measured spectra comprise absorbance spectra in the near infrared region.

21. The method of claim 20 wherein said predictive model is determined by a linear least squares regression.

22. The method of claim 19 wherein said process comprises a procedure chosen from the group consisting of: polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation; ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

23. The method of claim 20 wherein said process comprises a procedure chosen from the group consisting of polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation;

ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

24. The method of claim 20 wherein said set of orthonormal basis functions characterizing said corrected absorbance spectra for said calibration samples comprise eigenspectra determined by a Singular Value Decomposition.

25. The method of claim 21 wherein said set of orthonormal basis functions characterizing said corrected absorbance spectra for said calibration samples comprise eigenspectra determined by a Singular Value Decomposition.

26. The method of claim 22 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

27. The method of claim 23 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

28. The method of claim 23 wherein said measurement of near infrared spectra are made by a Fourier Transform Near Infrared (FTNIR) spectrometer.

29. The method of claim 25 wherein said measurement of near infrared spectra are made by a Fourier Transform Near Infrared (FTNIR) spectrometer.

30. The method of claim 24 wherein said measurement of said spectrum for said test sample is performed at least once every two minutes.

31. The method of claim 25 wherein said measurement of said spectrum for said test sample is performed at least once every two minutes.

32. A process plant to produce a product with a property P having a desired value D comprising:
   a first device for measuring a spectrum contaminated by measurement errors at at least one intermediate step in the process, to give a set of measured spectra for a set of calibration samples and for a test sample;
   a second device for measuring said value of said property P for each of said calibration samples; and
   a computer adapted to:
      correct said measured spectra of said calibrations samples and said test sample for measurement errors to give a set of corrected spectra;
      derive a predictive model relating said corrected spectra for said calibration samples to said measured value of said property P for said calibration samples;
      predict an expected value E for said property P of said test sample from said predictive model and said corrected spectra for said test sample; and
      control said process plant using a calculated difference between said expected value E and said desired value D.

33. The process plant of claim 32 wherein said product comprises a polymer.

34. The process plant of claim 32 wherein said measured spectra are selected from the group consisting of: Raman spectra, NMR spectra, and infrared spectra.

35. The process plant of claim 32 wherein said measured spectra comprise absorbance spectra in the near infrared region.

36. The process plant of claim 35 wherein said predictive model is determined by a linear least squares regression.

37. The process plant of claim 34 wherein said process comprises a procedure chosen from the group consisting of: polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation; ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

38. The process plant of claim 35 wherein said process comprises a procedure chosen from the group consisting of: polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation; ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

39. The process plant of claim 37 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

40. The process plant of claim 38 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

41. The process plant of claim 39 wherein said measurement of near infrared spectra are made by a Fourier Transform Near Infrared (FTNIR) spectrometer.

42. The process plant of claim 40 wherein said measurement of near infrared spectra are made by a Fourier Transform Near Infrared (FTNIR) spectrometer.

43. A process plant producing a product with a property P having a desired value D in a plurality of steps, the process plant comprising:
   a first device for measuring a spectrum contaminated by measurement errors at at least one intermediate step in the process, to give a set of measured spectra for a set of calibration samples and for a test sample;
   a second device for measuring said value of said property P for each of said calibration samples;
   a third device for obtaining a value of at least one additional property of said calibration samples and for said test sample; and
   a computer adapted to:
      correct said measured spectra of said calibrations samples and said test sample for measurement errors to give a set of corrected spectra;
      derive a predictive model relating said corrected spectra and said value of said at least one additional property for said calibration samples to said measured value of said property P for said calibration samples;
predict an expected value E for said property P of said test sample from the predictive model, said corrected spectra and said value of said at least one additional property for said test sample; and
control said process plant using a calculated difference between said expected value E and said desired value D.

44. The process plant of claim 43 wherein said at least one additional property is selected from the group of: temperature, viscosity, pressure, density, refractive index, pH value, conductance and dielectric constant.

45. The process plant of claim 43 wherein said product comprises a polymer.

46. The process plant of claim 43 wherein said spectra are selected from the group consisting of: Raman spectra, NMR spectra, and infrared spectra.

47. The process plant of claim 43 wherein said measured spectra comprise absorbance spectra in the near infrared region.

48. The process plant of claim 45 wherein said predictive model is determined by a linear least squares regression.

49. The process plant of claim 44 wherein said process comprises a procedure chosen from the group consisting of: polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation; ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

50. The process plant of claim 46 wherein said process comprises a procedure chosen from the group consisting of: polymerization; steam cracking; olefin purification; aromatic purification; isomerization; catalytic cracking; catalytic reforming; hydrogenation; oxidation; partial oxidation; dehydration; hydration; nitration; epoxidation; distillation; combustion; alkylation; neutralization; ammination; esterification; dimerization; membrane separation; carbonylation; ketonization; hydroformulation; oligomerization; pyrolysis; solfonation; crystallization; adsorption; extractive distillation; hydrodealkylation; dehydrogenation; aromatization; cyclization; thermal cracking; hydrodesulphurization; hydrodenitrogenation; peroxidation; deashing and halogenation.

51. The process plant of claim 47 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

52. The process plant of claim 48 wherein said property P is selected from the group consisting of: Mooney viscosity, polymer unsaturation, comonomer incorporation, halogen content, polymer concentration, monomer concentration, molecular weight, melt index, polymer density, stream component composition, moisture in the product, and molecular weight distribution.

53. The process plant of claim 51 wherein said measured near infrared spectra are made by a Fourier Transform Near Infrared (FTNIR) spectrometer.

54. The process plant of claim 50 wherein said near infrared spectra are measured by a Fourier Transform Near Infrared (FTNIR) spectrometer.

* * * * *